US009975646B2

(12) United States Patent
Jiao et al.

(10) Patent No.: US 9,975,646 B2
(45) Date of Patent: May 22, 2018

(54) AEROSPACE TRANSPARENCY HAVING MOISTURE SENSORS

(71) Applicant: PPG INDUSTRIES OHIO, INC., Cleveland, OH (US)

(72) Inventors: Yu Jiao, Blawnox, PA (US); Jeremy D. Acord, Lower Burrell, PA (US); Nicolas B. Duarte, Allison Park, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days. days.

(21) Appl. No.: 15/365,246

(22) Filed: Nov. 30, 2016

(65) Prior Publication Data
US 2017/0082572 A1    Mar. 23, 2017

Related U.S. Application Data

(63) Continuation-in-part of application No. 14/810,517, filed on Jul. 28, 2015.

(51) Int. Cl.
*G01R 27/08* (2006.01)
*B64D 45/00* (2006.01)
(Continued)

(52) U.S. Cl.
CPC .............. *B64D 45/00* (2013.01); *B60J 10/00* (2013.01); *B64C 1/1484* (2013.01); *B64D 15/20* (2013.01);
(Continued)

(58) Field of Classification Search
CPC ........ G01N 27/605; G01M 3/40; B64D 45/00
(Continued)

(56) References Cited

U.S. PATENT DOCUMENTS 2,681,571 A * 6/1954 Becker ............... G01N 27/4166
204/430
3,440,372 A    4/1969 Cecil
(Continued)

FOREIGN PATENT DOCUMENTS

JP      2007248409      9/2007
WO      8103709 A1      12/1981
(Continued)

OTHER PUBLICATIONS

Google Search—"Coaxial Moisture Sensor" on Apr. 16, 2015.

*Primary Examiner* — Arleen M Vazquez
*Assistant Examiner* — Steven Yeninas
(74) *Attorney, Agent, or Firm* — Neil J. Friedrich

(57) ABSTRACT

A transparency, e.g. an aircraft laminated windshield, includes one or more moisture sensors to monitor moisture penetration to monitor performance of the moisture barrier. At least one of the moisture sensors includes an electrolyte between and in ionic contact with two electrically conductive electrodes. Measuring the potential between the first and second electrode and/or the current through the electrodes to determine the amount of moisture within the laminated windshield in the area of the moisture sensor. With the information provided by the moisture sensors performance of the windshield is available to schedule timely repair or replacement of the windshield that is performing outside of acceptable limits.

23 Claims, 8 Drawing Sheets

(51) Int. Cl.
*B64C 1/14* (2006.01)
*B64D 15/20* (2006.01)
*G01N 27/12* (2006.01)
*G01R 27/26* (2006.01)
*B60J 10/00* (2016.01)
*G01M 3/16* (2006.01)
*G01N 27/416* (2006.01)
*G01N 27/42* (2006.01)

(52) U.S. Cl.
CPC ............ *G01M 3/16* (2013.01); *G01N 27/121* (2013.01); *G01N 27/4166* (2013.01); *G01R 27/2635* (2013.01); *G01R 27/2641* (2013.01); *G01R 27/2647* (2013.01); *B64D 2045/0085* (2013.01); *G01N 27/423* (2013.01)

(58) Field of Classification Search
USPC ............ 73/74, 75; 244/129.3; 324/664, 694; 340/604, 605
See application file for complete search history.

(56) References Cited

U.S. PATENT DOCUMENTS

| | | | |
|---|---|---|---|
| 3,771,349 A * | 11/1973 | Yatabe | G01M 3/16 73/29.05 |
| 4,078,107 A | 3/1978 | Bitterice et al. | |
| 4,352,059 A | 9/1982 | Suh et al. | |
| 4,522,060 A | 6/1985 | Murata et al. | |
| 4,610,771 A | 9/1986 | Gillery | |
| 4,623,389 A | 11/1986 | Donley et al. | |
| 4,704,174 A | 11/1987 | Valimont et al. | |
| 4,806,220 A | 2/1989 | Finley | |
| 4,820,902 A | 4/1989 | Gillery | |
| 4,894,513 A | 1/1990 | Koontz | |
| 4,902,875 A | 2/1990 | Koontz | |
| 4,994,650 A | 2/1991 | Koontz | |
| 5,028,906 A | 7/1991 | Moriya et al. | |
| 5,675,944 A | 10/1997 | Kerr et al. | |
| 5,821,001 A | 10/1998 | Arbab et al. | |
| 5,959,535 A * | 9/1999 | Remsburg | A61F 13/42 128/886 |
| 6,826,948 B1 * | 12/2004 | Bhatti | G01M 3/188 340/605 |
| 6,914,530 B2 * | 7/2005 | Geary | E02B 17/0034 340/604 |
| 7,586,664 B2 | 9/2009 | O'Shaughnessy | |
| 7,760,105 B2 * | 7/2010 | Turner | G08B 21/20 340/605 |
| 8,155,816 B2 | 4/2012 | Rashid et al. | |
| 2004/0089058 A1 * | 5/2004 | De Haan | G01N 27/225 73/73 |
| 2005/0115308 A1 | 6/2005 | Koram et al. | |
| 2007/0002422 A1 | 1/2007 | O'Shaughnessy | |
| 2010/0163675 A1 | 7/2010 | Rashid et al. | |
| 2011/0011179 A1 * | 1/2011 | Gustafsson | G01N 27/223 73/335.03 |
| 2015/0137837 A1 | 5/2015 | Jiao et al. | |
| 2015/0171624 A1 | 6/2015 | Duarte et al. | |

FOREIGN PATENT DOCUMENTS

| | | |
|---|---|---|
| WO | 2007009767 A2 | 1/2007 |
| WO | 2015073269 A1 | 5/2015 |

* cited by examiner

AEROSPACE TRANSPARENCY HAVING MOISTURE SENSORS

CROSS REFERENCE TO RELATED APPLICATIONS

This application is a continuation-in-part application of U.S. patent application Ser. No. 14/810,517 filed on Jul. 28, 2015 in the names of Jeremy Acord, Nicolas Duarte, and Yu Jiao for aerospace transparency having moisture sensors.

BACKGROUND OF THE INVENTION

Field of the Invention

This invention relates to transparencies, e.g. windows, having one or more moisture sensors to measure ingress of moisture, and more particularly, to aircraft and aerospace laminated windows, e.g. laminated windshield, having moisture sensors to monitor real time performance of moisture seals of the windshield, and the amount of moisture accumulated over a predetermined period of time.

Aircraft and aerospace windows, e.g. windshields include a laminate of plastic layers or sheets, glass layers or sheets and combinations thereof. The layers of an inner segment of the windshield face the interior of the aircraft and are designed to provide structural stability to the windshield. The layers of outer segment of the windshield face the exterior of the aircraft and are designed to provide structural stability and accessories for visual acuity. For example and not limiting to the discussion, one accessory to enhance visual acuity is a heatable member that includes an electrically conductive coating, or a plurality of electrically conductive wires, between and connected to a pair of spaced bus bars to heat the outer surface of the windshield to prevent the formation of, and/or to remove fog and ice on and/or from, respectively, the outer surface of the windshield.

Description of Related Art

As is appreciated by those skilled in the art, as the service time of the aircraft windshield increases, the operating efficiency of the windshield decreases until such time that the windshield becomes non-functional, and the windshield needs to be replaced or repaired. More particularly, the peripheral edge of the windshield has an outboard moisture seal that is a barrier to prevent moisture from entering between the plastic and glass layers or sheets of the windshield. When the moisture seal fails, e.g. cracks and/or the layers of the windshield laminate de-bond, moisture enters between the layers of the windshield. While the cracking or de-bonding of the seal is not a structural issue, when moisture moves between the layers of the windshield, the windshield can de-laminate, and the conductive coating or wires, whichever is present can be damaged and fail, thereby reducing or ending, the service life of the windshield. More particularly, when delamination of the windshield occurs, increased amounts of moisture move between the layers of the windshield accelerating the degradation of the windshield, e.g. damage and/or failure of the bus bars and electrically conductive coating or wires, which reduces or eliminates the defrosting capabilities of the windshield.

Untimely response to repair defects in the accessories of the transparency when they begin, decreases the operating efficiency of the transparency and can result in the need for emergency maintenance, e.g. the repair or replacement of the transparency. It would be advantageous, therefore, to provide a transparency with moisture sensors to monitor the performance of the transparency so that the repair, or replacement, of the transparency is a scheduled maintenance and not an emergency maintenance.

SUMMARY OF THE INVENTION

This invention relates to a transparency, e.g. but not limited to an aircraft windshield having, among other things, a plurality of sheets joined together to provide a laminated windshield having a vision area, the window having a moisture seal on the peripheral and marginal edge portions of the sheets. A moisture sensor is positioned between the sheets and/or between the sheets and the moisture seal. The moisture sensor includes, among other things, an electrolyte member between a first electrode and a second electrode wherein the electrolyte material is in electrical contact with the first and second electrodes and maintains the first and the second electrodes spaced from one another and out of the surface contact with one another. Sensor electronics are operatively connected to the electrodes of the moisture sensor to measure an electrical property of the sensor to determine amount of moisture absorbed by the electrolyte member, wherein the electrical potential between the electrodes and/or current supplied through a calibrated load within the sensor electronics measures the amount of moisture within the laminated windshield in the area of the moisture sensor.

The invention further relates to a method of making the aircraft transparency having a moisture sensor. The method includes, among other things, fabricating a laminated aircraft transparency having a moisture barrier over the outer surface of the marginal edges of, and periphery of the laminated aircraft transparency. During fabrication of the laminated aircraft transparency, a sensor element responsive to moisture is placed between the sheets and/or between the sheets and the moisture seal of the aircraft transparency. In one non-limiting embodiment of the invention, the sensor element includes, among other things, an electrolyte member between a first electrode and a second electrode wherein the electrolyte material is in ionic contact with the first and second electrodes and maintains the first and the second electrodes spaced from one another and out of contact with one another, wherein the electrical potential between the electrodes is measured and/or current supplied through a calibrated load within the sensor electronics is measured to determine the amount of moisture within the laminated windshield in the area of the moisture sensor.

DESCRIPTION OF THE INVENTION

Figure 1:
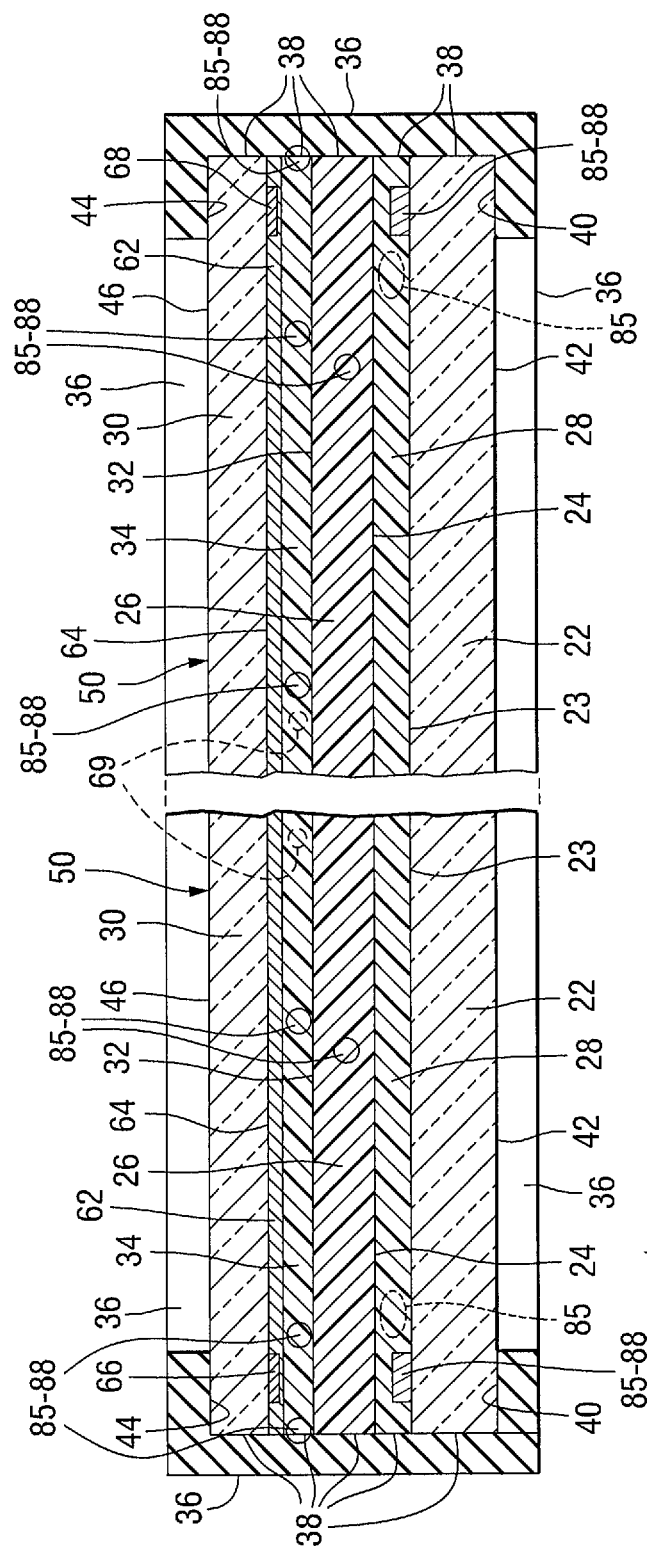
FIG. 1 is a cross sectional view of a non-limiting embodiment of an aircraft windshield incorporating features of the invention.

As used herein, spatial or directional terms such as "inner", "outer", "left", "right", "up", "down", "horizontal", "vertical", and the like, relate to the invention as it is shown in the drawing on the figures. However, it is to be understood that the invention can assume various alternative orientations and, accordingly, such terms are not to be considered as limiting. Further, all numbers expressing dimensions, physical characteristics, and so forth, used in the specification and claims are to be understood as being modified in all instances by the term "about". Accordingly, unless indicated to the contrary, the numerical values set forth in the following specification and claims can vary depending upon the property desired and/or sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Moreover, all ranges disclosed herein are to be understood to encompass any and all subranges subsumed therein. For example, a stated range of "1 to 10" should be considered to include any and all subranges between and inclusive of the minimum value of 1 and the maximum value of 10; that is, all subranges beginning with a minimum value of 1 or more and ending with a maximum value of 10 or less, e.g., 1 to 6.7, or 3.2 to 8.1, or 5.5 to 10. Also, as used herein, the term "applied over", "positioned over" or "mounted over" means applied on, positioned on or mounted over but not necessarily in surface contact. For example, one article or component of an article "applied over", "mounted over" or "positioned over" another article or component of an article does not preclude the presence of materials between the articles, or between components of the article, respectively.

Before discussing several non-limiting embodiments of the invention, it is understood that the invention is not limited in its application to the details of the particular non-limiting embodiments shown and discussed herein since the invention is capable of other embodiments. Further, the terminology used herein to discuss the invention is for the purpose of description and is not of limitation. Still further, unless indicated otherwise, in the following discussion like numbers refer to like elements.

Non-limiting embodiments of the invention are directed to an aircraft laminated transparency, and in particular to an aircraft laminated windshield. The invention, however, is not limited to any particular type of aircraft transparency, and the invention contemplates the practice of the invention on any type of windshield, e.g. but not limited to (1) a laminated windshield disclosed in U.S. Pat. No. 8,155,816; (2) an aircraft window having a medium responsive to electric stimuli to increase or decrease visible transmission, e.g. but not limited to the type of aircraft window disclosed in U.S. Pat. No. 7,586,664 and (3) aircraft windows of the type having an insulated air space between a pair of laminated sheets. Further, the invention can be practiced on commercial and residential windows, e.g. but not limited to (1) the type disclosed in U.S. Pat. No. 5,675,944; (2) a window for any type of land vehicle; (3) a canopy, cabin window and windshield for any type of air and space vehicle; (4) a window for any above and/or below water vessel, and (5) a window for a viewing side or door for any type of containers, for example but not limited to a refrigerator, cabinet and/or oven door. The documents identified herein are hereby incorporated by reference. Still further, the invention is not limited to the material of the layers or sheets of the transparency, and the layers or sheets can be made of, but not limited to, cured and uncured plastic sheets; annealed glass sheets, and heat and chemically strengthened, clear, colored, coated and uncoated glass sheets The laminated windshield is usually designed to be a passive component of the aircraft with de-icing and/or de-fogging features. In the practice of the non-limiting aspects of the invention, sensors are used to provide feedback on the performance of the transparency. More particularly, the moisture sensors of the invention provide an intelligent window with the goal of providing feedback on the health status of the window system for electrical and mechanical integrity. Specifically, moisture ingress is a known problem of aerospace transparency aging, especially when window seals are not properly maintained. If moisture ingress is left to continue, the moisture ingress can permanently deteriorate the interior laminate, causing reduced visibility and rendering the window useless. In the worst cases, moisture ingress can affect the electrically conductive heater layer (discussed in detail below), potentially causing arcing and structure failure of one or more layers, sheets or plies of the laminated windshield.

Shown in FIG. 1 is a non-limiting embodiment of an aircraft windshield 20 that can be used in the practice of the invention. The windshield 20 has a first glass sheet 22 secured to surface 24 of a vinyl-interlayer or sheet 26 by a first urethane interlayer 28, and has a second glass sheet 30 secured to surface 32 of the vinyl-interlayer 26 by a second urethane interlayer 34. An edge member or moisture barrier 36 of the type used in the art, e.g. but not limited to a silicone rubber or other flexible durable moisture resistant material is secured to (1) peripheral edge 38 of the windshield 20, i.e. the peripheral edge 38 of the first and second sheets 22 and 30, respectively; of the vinyl-interlayer 26; of the first and second urethane interlayers 28 and 34, respectively; (2) margins or marginal edges 40 of outer surface 42 of the windshield 20, i.e. the margins 40 of the outer surface 42 of the first glass sheet 22 of the windshield 20, and (3) margins or marginal edges 44 of outer surface 46 of the windshield 20, i.e. margins of the outer surface 46 of the second glass sheet 30.

As is appreciated by those skilled in the art and not limiting to the invention, the first glass sheet 22; the vinyl-interlayer 26 and the first urethane interlayer 28 form the structural part, or the inner segment, of the windshield 20. The outer surface 42 of the windshield 20, which is the outer surface 42 of the glass sheet 22 faces the interior of the vehicle. The type of vehicle is not limited to the invention e.g. but not limited to an aircraft of the type shown in U.S. Pat. No. 8,155,816 B2, which patent in its entirety is hereby incorporated by reference. The second urethane layer 34 and the second glass sheet 30 form the non-structural part, or outer segment, of the windshield 20. The outer surface 46 of the windshield 20, which is the surface 46 of the second glass sheet 30 faces the exterior of the aircraft. The second glass sheet 30 is part of a heatable member 50 that provides heat to remove fog from, and/or to melt ice on, the outer surface 46 of the windshield 20 in a manner discussed below.

As can be appreciated, the invention is not limited to the construction of the windshield 20 and any of the constructions of aircraft transparencies disclosed in the art can be used in the practice of the invention. For example and not limiting to the invention, the windshield 20 can include a construction wherein the vinyl interlayer 26 and the first urethane interlayer 28 are omitted, and the glass sheets 22 and/or 30 are plastic sheets.

Generally the glass sheets 22 and 30 of the windshield 20 are clear chemically strengthened glass sheets; however, the invention is not limited thereto, and the glass sheets 22 and/or 30 can be heat strengthened or heat tempered glass sheets. Further as is appreciated, the invention is not limited to the number of glass sheets, vinyl interlayers and/or urethane interlayers that make up the windshield 20, and the windshield 20 can have any number of sheets and/or interlayers.

Figure 2:
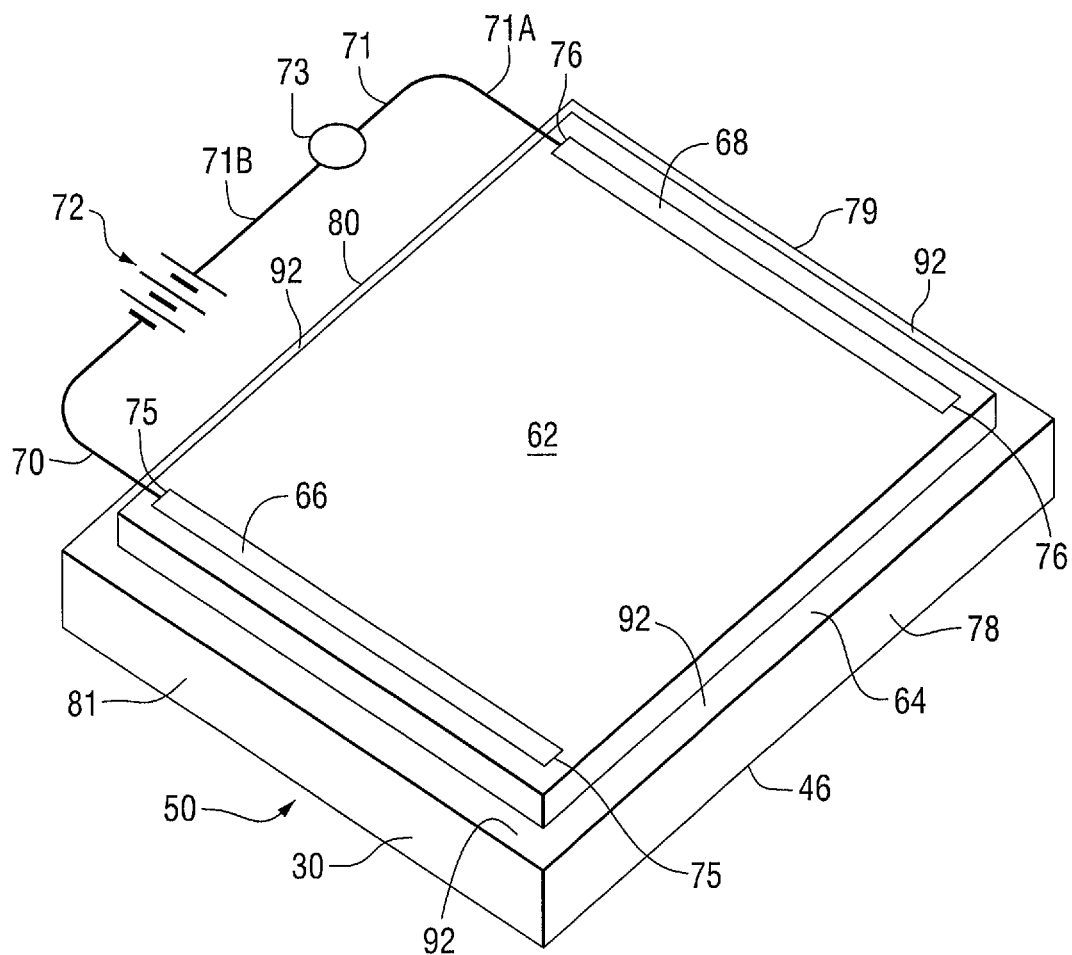
FIG. 2 is an isometric view of a prior art heatable member for removing fog, and melting ice and snow on the outer surface of the windshield.

The invention is not limited to the design and/or construction of the heatable member 50, and any electrically conductive heatable member used in the art to heat a surface of a glass and plastic sheets to melt ice on, and/or remove fog from, the surface of the sheet can be used in the practice of the invention. With reference to FIG. 2, in one non-limiting embodiment of the invention, the heatable member 50 includes a conductive coating 62 applied to surface 64 of the second glass sheet 30, and a pair of spaced bus bars 66 and 68 in electrical contact with the conductive coating 62. The invention is not limited to the composition of the conductive coating 62, for example and not limiting to the invention; the conductive coating 62 can be made from any suitable electrically conductive material. Non-limiting aspects of conductive coatings that can be used in the practice of the invention include, but are not limited to a pyrolytic deposited fluorine doped tin oxide film of the type sold by PPG Industries, Inc. under the trademark NESA®; a magnetron sputter deposited tin doped indium oxide film of the type sold by PPG Industries, Inc. under the trademark NESATRON®; a coating made up of one or more magnetron sputter deposited films, the films including, but not limited to a metal film, e.g. silver between metal oxide films, e.g. zinc oxide and/or zinc stannate, each of which may be applied sequentially by magnetron sputtering, e.g. as disclosed in U.S. Pat. Nos. 4,610,771; 4,806,220 and 5,821,001, the disclosures of which in their entirety are hereby incorporated by reference.

As can be appreciated, the invention is not limited to the use of an electrically conductive coating to heat the glass sheet 60 and contemplates the use of any type of member that can be electrically heated, e.g. but not limited to electrical conducting wires. The wires, e.g. the wires 69 shown in phantom in FIG. 1 can be embedded in the second urethane interlayer 34 and electrically connected to the bus bars 66 and 68. Such a heating arrangement is known in the art under the PPG Industries Ohio Inc. registered trademark AIRCON and is disclosed in U.S. Pat. No. 4,078,107, which patent in its entirety is incorporated herein by reference. Further, as can be appreciated by those skilled in the art, the invention can be practice on laminated articles, e.g. but not limited to, windows that do not have heatable members.

The invention is not limited to the design and/or construction of the bus bars and any of the types of bus bars known in the art can be used in the practice of the invention. Examples of bus bars that can be used in the practice of the invention, include, but are not limited to, the types disclosed in U.S. Pat. Nos. 4,623,389; 4,820,902; 4,894,513; 4,994,650, and 4,902875, which patents in their entirety are hereby incorporated by reference. Each of the bus bars 66 and 68 are connected by a wire 70 and 71, respectively to a power source 72, e.g. a battery to flow current through the bus bars 66 and 68, and the conductive coating 62 to heat the conductive coating 62 and the second glass sheet 30 to remove ice and/or fog from the outer surface 46 of the windshield 20. A window heat controller 73 to provide electrical current to heat the coating 62 and to disconnect electrical current from the coating 62 is connected to one of the wires, e.g. the wire 71 such that wire section 71A of the wire 71 connects one pole of the window heat controller 73 to the bus bar 68, and the wire section 71B of the wire 71 connects another pole of the window heat controller 73 to the battery 72. With this arrangement, the window heat controller 73 can control the electrical power to the bus bars 66 and 68, and the conductive coating 62 to vary and/or regulate the current flow through the bus bars 68 and 66, and the conductive coating 62 to control the temperature of the conductive coating 62. Although not limiting to the invention, ends 75 of the bus bar 66, and ends 76 of the bus bar 68 are spaced from adjacent sides 78-81 of the glass sheet 30 to prevent arcing of the bus bars 66 and 68 with the metal body cover of the aircraft (shown in U.S. Pat. No. 8,155,816B2).

Figure 3:
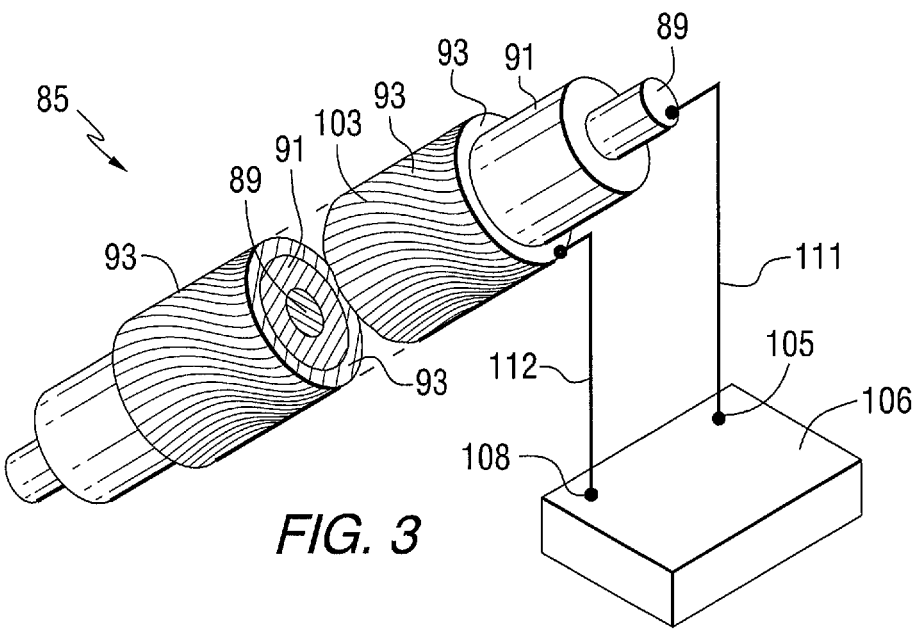
FIG. 3 is an isometric segmented view of a non-limiting aspect of a moisture sensor or detector of the invention.

Shown in FIGS. 3-6 are non-limiting embodiments of moisture sensors 85-88, respectively, of the invention. With reference to FIG. 3, the moisture sensor 85 has a coaxial arrangement and includes, but is not limited to, a central electrical conductor 89, an electrolyte sleeve 91 over the central electrode 89, and an outer moisture pervious electrical conductive electrode 93.

In the preferred practice of the invention, but not limiting the invention thereto, one of the electrodes of the moisture sensor 85 is a cathode 89, and the electrode 93 is an anode 93. As can now be appreciated the invention contemplates the electrode 89 as the cathode 93. Unless indicated otherwise in the discussion below the electrode 89 is an anode 89 and the electrode 93 is the cathode 93.

Figure 4:
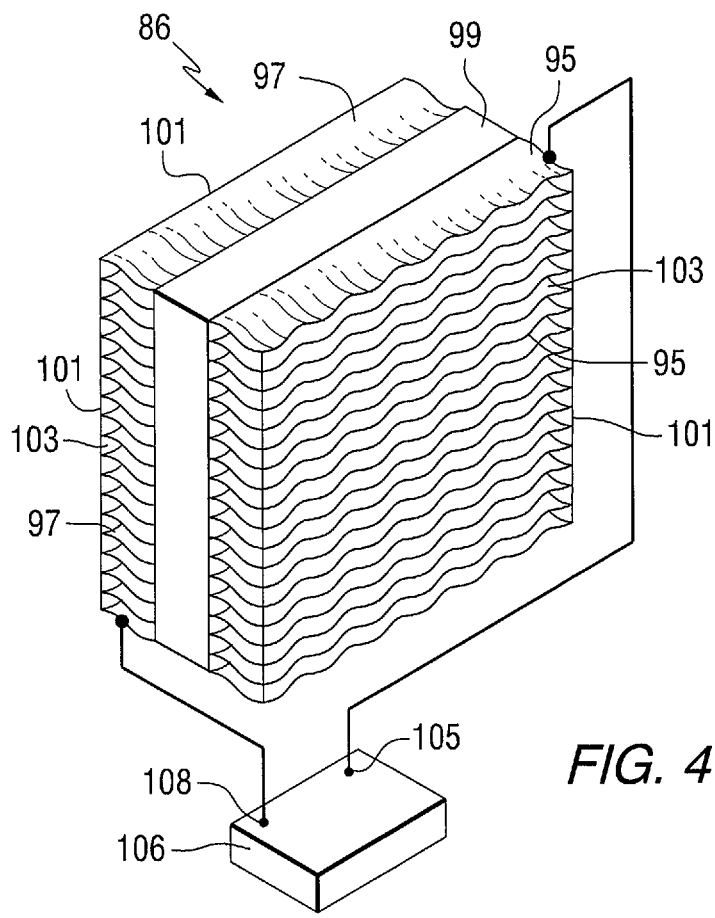
FIG. 4 is an isometric view of another non-limiting aspect of a moisture sensor or detector of the invention.

The moisture sensor 86 shown in FIG. 4 includes a first outer moisture porous electrical conductive electrode 95 spaced from a second outer moisture porous electrical conductive electrode 97, and an electrolyte layer 99 between and in physical and ionic contact with the first and second electrodes 95 and 97, respectively. In the practice of the invention, one of the electrodes 95 and 97 is an anode and the other electrode 97 and 95 is a cathode. For purposes of clarity and not limiting to the invention unless indicated otherwise the electrode 97 is the anode 97, and the electrode 95 is the cathode 95.

The electrolyte 91 of the moisture sensor 85 (see FIG. 3) and the electrolyte 99 of the moisture sensor 86 (see FIG. 4) used in the practice of the invention is an electrolyte that is compatible with wire manufacturing, with preferably a large saturated moisture capacity, and with a melting temperature greater than the laminate processing temperature for the windshield 20 (see FIG. 1). Electrolytes that can be used in the practice of the invention include but are not limited to materials that absorb moisture to form an ionically conductive medium that can be used in their pure form or interspersed within a matrix selected to provide the required mechanical properties. As is appreciated by those skilled in the art, in the ideal but non-limiting embodiment the electrolyte will have high ionic conductivity and low electronic conductivity. In the ideal but non-limiting embodiment the electrolyte will not form an ionic conductor in the absence of moisture, and the specific electrolyte and/or matrix materials can be selected to alter the moisture content of the interlayer at which the electrolyte becomes ionically conductive. Examples of such electrolytes can include but are not limited to acids, such as sulfuric, hydrochloric, phosphoric, nitric, carboxylic (such as adipic, mallic, acetic, but not limited by the organic ligands of the acid), and bases, such as sodium hydroxide, potassium hydroxide, lithium hydroxide, magnesium hydroxide, calcium hydroxide. Salts formed by reactions between said acids and bases can be added to alter the rate of reaction between the electrolyte and the anode and the moisture content of the interlayer at which the electrolyte first forms an ionically conductive medium. The electrolyte properties can also be engineered by addition of modifies including, but not limited to, rheology modifiers such as a thickeners or gelling agents, gassing control agents, buffers, deliquescent salts, etc. The mixture of the electrolyte with any aforementioned matrix or modifying compounds in their plurality will be referred to hereinafter as the electrolyte, and wherever used in this document the word electrolyte will be understood to the potential for such plurality. The matrix can consist of a thermoplastic polymer or other material compatible with wire manufacturing that can contain the electrolyte within pores forming the matrix material, and may also include a gelling agent to cause the aqueous electrolyte to remain substantially within the confines of the matrix material.

This invention is not limited by the means by which the matrix materials can be formed, but can include, as a non-limiting example, blending of an electrolyte that in the dehydrated state forms a solid, which solid having been milled to a consistency compatible with extrusion during the wire manufacturing process, and which may be manufactured, stored, transported and processed in the dry state. Alternatively a process to create a network of interconnected voids within the body of the matrix material can be used, and the voids subsequently infiltrated with the electrolyte, and dried prior to installation as a sensor unit in the window.

Figure 5:
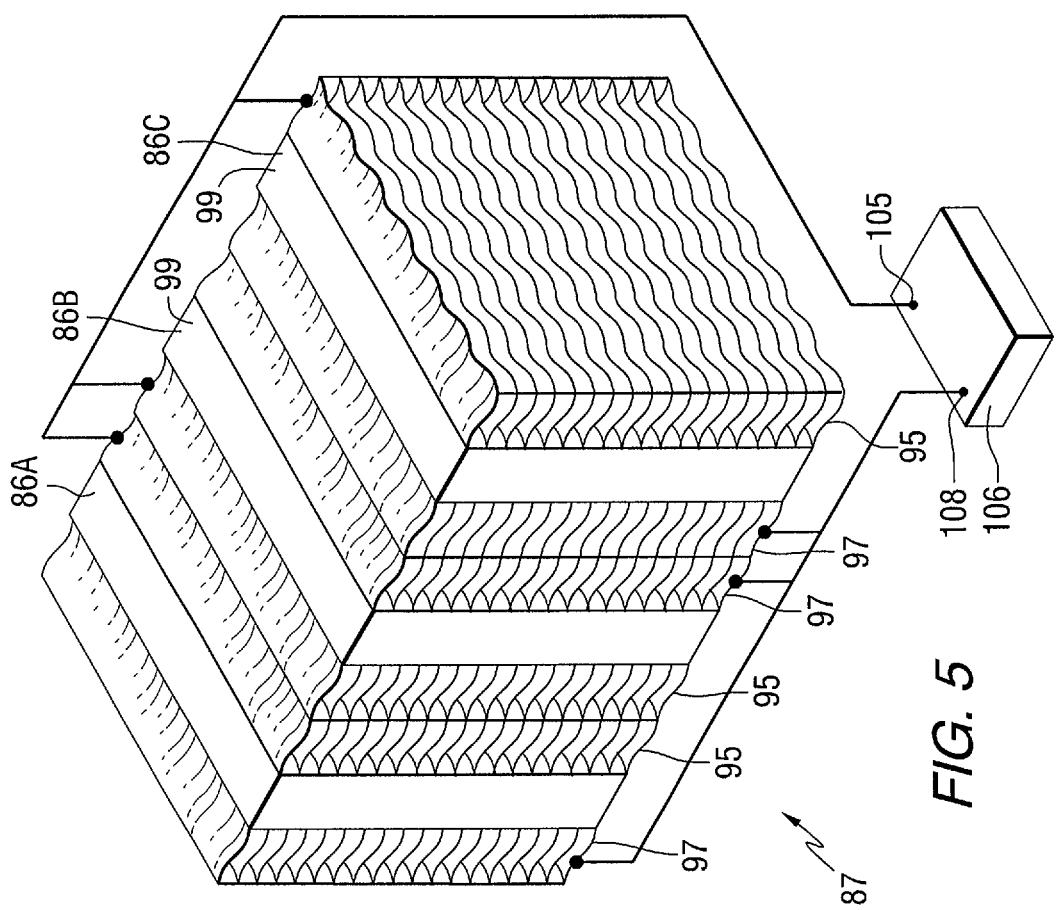
FIG. 5 is an isometric view of still another non-limiting aspect of a moisture sensor or detector of the invention.
Figure 6:
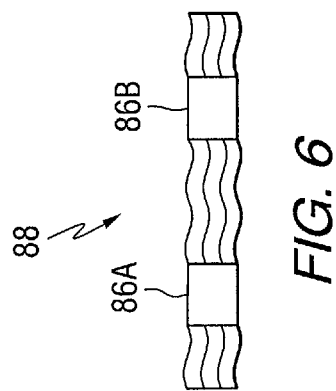
FIG. 6 is a cross sectional view of a segment of a non-limiting aspect of a moisture sensor or detector of the invention.

The moisture sensors 85 and 86 shown in FIGS. 3 and 4, respectively, can also include any number of additional moisture permeable conducting or insulating layers that do not substantially change the electrical response of the moisture sensor but can be desirable for fabrication or installation of the sensor. Shown in FIG. 5 is the moisture sensor 87 that is a stacking of a plurality of moisture sensors 86 shown in FIG. 4 to increase the measurable current of the moisture sensor 86 of FIG. 4. With reference to FIGS. 4 and 5, as needed, the moisture sensor 87 is shown as a stack of the moisture sensors 86. As shown in FIG. 6, the moisture sensor 88 is designated 86A for the extreme left moisture sensor, and 86B for the extreme right moisture sensor. The anode 97 of the moisture sensor 86A provides the left end of the moisture sensor 87. The cathode 95 of the moisture sensor 86A and the cathode 95 of the moisture sensor 86B are electrically connected in any manner. The cathode 95 of the moisture sensor 86B provides the right end of the moisture sensor 87 as viewed in FIG. 6.

The moisture sensor 87 shown in FIG. 5 can be made by connecting adjacent anodes or cathodes as discussed above. However, as is appreciated by those skilled in the art, the width of the anode or cathode can be increased by extending the width of the anode or cathode (see FIG. 6) to eliminate the need to connect adjacent moisture sensors. The width of the anode and cathode is defined as the distance between adjacent electrolytes 99.

Shown in FIGS. 5 and 6 as needed is the moisture sensor 88 that is a stacking of a plurality of moisture sensors 86 shown in FIG. 4 to increase the measurable potential of the moisture sensor 86 of FIG. 4. With reference to FIGS. 4 and 5, as needed, the moisture sensor 87 is shown as a stack of the moisture sensors 86. As shown in FIG. 4, the moisture sensors 88 are designated 86A for the extreme left moisture sensor, and 86B for the extreme right moisture sensor. The anode 97 of the moisture sensor 86A provides the left end of the moisture sensor 87. The cathode 95 of the moisture sensor 86A and the anode 97 of the moisture sensor 86B are electrically connected in any manner. The cathode 95 of the moisture sensor 86B and the anode 97 of the moisture sensor 86A are electrically connected in any manner. The cathode 95 of the moisture sensor 86B provides the right end of the moisture sensor 88.

The moisture sensors 85-88 are made of materials that are non-reactive with the materials of the windshield, e.g. but not limited to the glass sheets 22 and 30, the conductive coating 62, the vinyl interlayer 26 and the urethane interlayers 28 and 34. More particularly, the anode 89 and the cathode 93 of the moisture sensor 85, and the anode 97 and the cathode 95 of the moisture sensor 87 of the moisture sensor 86 are made of electrically conductive materials having a constant electrical conductivity over time at a fixed temperature. Further in the practice of the invention the anode and the cathode are made of different materials, e.g. different metals. Materials that can be used for the anode 89 and the cathode 93 of the moisture sensor 85, and the anode 97 and the cathode 95 of the moisture sensor 86, of the invention are found, among other places, in commonly published tables of galvanic series, also known as an electropotential series. Metals that can be used as anodes and cathodes in the practice of the invention include, but are not limited to, ruthenium, rhodium, palladium, silver, osmium, iridium, platinum, and gold, and non-noble metals and alloys such as, but not limited to, titanium, chromium, nickel, molybdenum, iron, copper, lead, tin, aluminum, zinc, magnesium, and alloys thereof. For purposes of the galvanic series elemental carbon in the form of graphite, carbon black, carbon fiber or graphene can be considered as a metal and used in the elemental form or as an alloying element with any of the metals previously listed.

The anode 89 and the cathode 93 of the moisture sensor 85 (FIG. 3); and the anode 97 and the cathode 95 of the moisture sensor 86 (FIG. 4), are preferably made of materials with differing electronegativity, e.g. different metals. In one aspect of the invention, the anode 89 of the moisture sensor 85 shown in FIG. 3 and the anode 97 of sensor 86 in FIG. 4 is made of a solid or stranded zinc or zinc-nickel alloy wire, and the cathode 93 of the moisture sensor 85 (see FIG. 3), and the cathode 95 of the moisture sensor 86 (see FIG. 4) are made of woven carbon fibers and are provided with passageways 103 to move moisture through the cathode 93 of the moisture sensor 85, and to move moisture through the cathode 95 of the moisture sensor 86 (FIG. 4), to contact the electrolyte material 91 between the electrodes 89 and 93 of the sensor 85, and to move through the outer cathode 95 and anode 97 of the sensor 86 to contact the electrolyte layer 99 between the anode 97 and cathode 95 of the moisture sensor 86. The invention is not limited to the thickness, size and number of passageways in the braid of the cathode 93 (FIG. 3) and 95 (FIG. 4) and the anode 97 (FIG. 4).

The electrolyte material 91 of the sensor 85 and the electrolyte material 99 of the sensor 87 used in the practice of the invention includes a porous battery separator to provide mechanical support and prevent electrical contact between the anode 89 and the cathode 93 of the moisture sensor 85 (FIG. 3), and between the anode 97 and the cathode 95 of the moisture sensor 86 (FIG. 4). The electrolyte is preferably a weak organic acid that forms a solid in a dry state, and that is chemically compatible with nylon, such as citric acid. The acid is preferably mixed with a deliquescent salt, such as the chlorides of lithium, calcium, magnesium, zinc, or any combination thereof, to enhance the sensor affinity for water and reduce the detection limit for water in the interlayer. The selection of deliquescent salt or absence thereof does not limit the scope or utility of the invention. When prepared from powders as a dried mixture the blended salt and electrolyte mixture can be further blended with any of the commonly available gelling agents compatible with the electrolyte chemistry, such as fumed silica or polyvinyl alcohol (PVA). The selection of gelling agent or absence thereof does not limit the scope or utility of the invention. The gelling agent is preferentially selected to increase the viscosity of the hydrated electrolyte to decrease the likelihood of a leak in the event of cracking and/or delamination of the sensing element, the windshield, or any components thereof.

Figure 7:
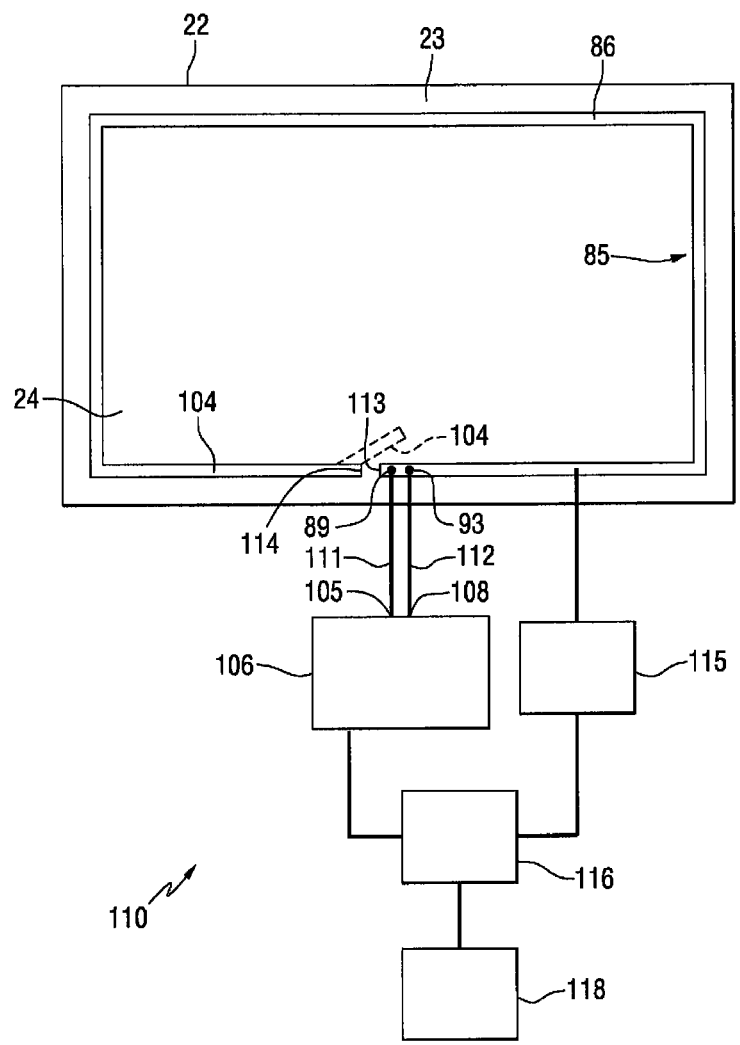
FIG. 7 is a plan view of an electrical system to monitor and act on the output signals of the moisture sensor of the invention in accordance to the teachings of the invention.

The potential developed by the sensor from the group of sensors 85-88 and/or the current through a calibrated load is measured by the electrical measurement mechanism 115 (see FIG. 7). As appreciated by those skilled in the art, the combination of anode 89 and the cathode 93 of the moisture sensor 85 (FIG. 3), and the anode 97 and the cathode 95 of the moisture sensor 86 (FIG. 4), together with the electrolyte 91 in FIG. 3 or 99 in FIG. 4 include the elements of an electrochemical cell. When fabricated as described above, and installed in the dried state, the electrochemical cell does not produce any appreciable voltage or current until water is introduced into the vicinity of the sensing element. When sufficient water reaches the vicinity of the sensing element the electrolyte will absorb the water, forming an ionic conductor. At that time a potential characteristic of the materials selected during sensor fabrication will appear between the anode 89 and the cathode 93 of the moisture sensor 85 (FIG. 3), and the anode 97 and the cathode 95 of the moisture sensor 86 (FIG. 4), and the anode and cathode of the moisture sensors 87 and 88. As appreciated by those skilled in the art, the total electrical response (current or voltage) generated by the sensor and passing through the electrical measurement mechanism 115 (see FIG. 7) is proportional to the extent of reaction at the anode 89 of the moisture sensor 85 (FIG. 3) and anode 97 of the moisture sensor 86 (FIG. 4). Moisture permeation into the electrolyte 91 in FIG. 3 or 99 in FIG. 4 primarily causes an increase in the volume of electrolyte that conducts ions, and thus the total area of the anode 89 of the moisture sensor 85 (FIG. 3) and anode 97 of the moisture sensor 86 (FIG. 4) undergoing electrochemical reaction at the time of measurement. If all moisture is subsequently removed from the vicinity of the sensing element the electrochemical reaction will stop as the electrolyte will cease to conduct ions. The history of the potential and current generated by the sensing element as measured by electrical measurement mechanism 115 represents the duration and quantity of water present in the interlayer in the vicinity of the sensing element up to the time of the measurement. Similarly, through the use of a calibration routine the moisture content of the sensor 85 and/or 86 can be related to the moisture content of the materials in immediate contact with the sensor, such as the vinyl interlayer 26 or the urethane interlayers 28 and/or 34.

The thickness of the moisture sensors 85-88 is not limiting to the invention, however, in the practice of the invention, when the moisture sensors 85-88 are positioned between sheets, the thickness of the moisture sensors 85-88 is preferably limited to a thickness such that the moisture sensor can be positioned within a layer spaced from the layer on each side of the moisture sensor. In one non-limiting example, with reference to FIG. 1, the moisture sensors 85-88 shown in FIG. 3 are positioned in the plastic laminate layer 26, 28 and/or 34; the first urethane layer 28 having a thickness of 0.060 inch as measured between the surface 23 of the first glass sheet 22 and the surface 24 of the vinyl interlayer 26. The moisture sensor 85 preferably has a diameter of less than 0.060 inch, or the moisture sensor 86 has a thickness measured between outer surface 101 of the anode 97, and the anode 97 of the moisture sensor 87 to secure the moisture sensor 85 or 87 in the first urethane layer 28. As can be appreciated, when the moisture sensors 85-88 are placed on the periphery 38 of the windshield 20 within the moisture seal 36 (see FIG. 1), the thickness of the moisture sensors 85-88 is less than the thickness of the windshield as measured between the inner surface 42 and the outer surface 46, of the windshield 20 (see FIG. 1).

The discussion is now directed to fabricating the moisture sensor 85 (see FIG. 3). In one non-limiting example, the center anode 89 is made of 28 AWG 7/36 stranded zinc-nickel alloy wire. The electrolyte sleeve 91 is made of extruded specialty blended nylon loaded with powdered solid electrolyte mix, consisting of fumed silica, powdered citric acid and powdered zinc chloride. The electrolyte 91 has a wall thickness of 0.005 inch. The cathode 93 is made of carbon fiber braid, braided over the dielectric sleeve 91 with a nominal 90% coverage. An outer insulating layer (numbered 88 and shown only in FIG. 4 and only in phantom) consisting of Aegis H55WC Nylon Jacket Compound extruded over the braid to a nominal outside diameter of 0.045 inch. A moisture sensor 86 is also made. The electrolyte 99 of the moisture sensor 86 has a range of thicknesses from 0.001 inch to 0.032 inch with a non-limiting width of 0.5 inch. The length varies depending on the size of the windshield and the area to be monitored by the moisture sensor. In another non-limiting example of the invention, the electrolyte layer 99 of the sensor 86 consists of the same electrolyte material used for the electrolyte sleeve 91 of the moisture sensor 85 (see FIG. 3) absorbed in a glass mat. The anode 97 of the moisture sensor 86 is made of perforated zinc foil and the cathode 95 of the moisture sensor 86 is made of carbon tape, nominally 0.25 inch wide. The anode 95 and the cathode 97 of the moisture sensor 86 is joined to one pair of opposite surfaces of the electrolyte material 99 through lamination in a moisture permeable polymer sleeve.

As is appreciated by those skilled in the art, an electrolyte is a substance that produces an ionically conducting solution when dissolved in water. In the practice of the invention the electrolyte is preferably but not limiting to the invention water free in the initial state to have a base value of zero volts. As moisture moves through the electrolyte, a potential is expressed between the anode and the cathode. The voltage remains approximately constant as the electrolyte absorbs additional water, and gradually decreases over time as the anode is consumed by the electrochemical reaction. The current expressed by the sensor through a calibrated load increases as the electrolyte absorbs additional water, and eventually also decreases as the anode is consumed by the electrochemical reaction. Once the moisture starts to ingress into the windshield layer system, the electrical response of the sensors will be connected to additional electronics and/or sensors that will monitor for the potential and/or current and will detect these changes.

As can now be appreciated, the invention contemplates switching the positions of the anode and the cathode. More particularly, the electrode 89 of FIG. 3 identified as the anode can function as the cathode, provided the cathode 93 of FIG. 3 functions as the anode. This can be accomplished by fabricating the electrode 89 from the cathodic metal, for example carbon fiber, and the anode 93 from the anodic metal, for example, zinc-nickel alloy.

In the coaxial structure (FIG. 3) or the stripline structure (FIG. 4) the "outside insulation" represents the material matrix in which the sensor is embedded. For instance the outside insulation can consist of inter layer resin or material that surround the laminate. The wire mesh comprising the outer electrode of the coaxial pair was selected for moisture permeability, electrical conductivity and chemical electronegativity. The central conductor in the preferred practice of the invention is selected primarily for electrical conductivity and chemical electronegativity. The electronegativity of the anode relative to the cathode and the chemical composition of the electrolyte is selected to provide a measurable signal from the sensing element while minimizing the detection limits and optimizing chemical compatibility with the windshield system and the longevity of the sensing element following moisture detection. The moisture to be sensed moves from the outside insulation through the outer conductor and into the electrolyte. The coaxial geometry of the moisture sensor 85 (see FIG. 3) has the additional advantage of superior immunity to electrical interference, relative to the stripline geometry of the moisture sensor 87 (see FIG. 4) since the wire mesh can be held at aircraft ground or floating ground potential to provide electrical shielding of the anode 89 of the moisture sensor 85.

The purpose of the moisture measurement is not simply to measure the instantaneous water ingression rate between sheets of the aircraft laminated windshield, but also the quantity of moisture accumulated over time. The history of the moisture ingression is just as important as the absolute concentration of the water in the window system. The concept of the window moisture measurement is based on the electrical property changes of a sensor element following moisture ingression between the sheets of the windshield. A sensor system includes, but is not limited to, the moisture sensor together with the electrical power supply, circuitry and software that detects the changes and communicates the changes to the persons responsible for maintaining the aircraft in a safe operating condition, e.g. as disclosed in U.S. Pat. No. 8,155,816B2, which patent is hereby incorporated by reference.

In one non-limiting embodiment of the invention, the moisture sensor 85 and/or 86 is based on the predictable increase in potential resulting from the electrolyte sleeve 91 of the sensor 85 or the electrolyte 99 of the sensor 86 absorbing moisture. More particularly, the cathode 89 as shown in FIG. 3 is connected to one pole 105 of a potentiometer or ammeter 106, and the anode 93 is connected to a second pole 108 of the potentiometer 106 (see FIG. 7). As for the moisture sensor 86, the cathode 95 is connected to the pole 108 of the potentiometer 106, and the second outer electrode 97 is connected to the pole 108 of the potentiometer 106. The voltage expressed by the electrochemical cell on the electrodes is measured. As the electrolyte absorbs moisture above the threshold determined by the material choices the voltage between the anode and the cathode increases from near zero to a characteristic voltage determined by the materials selections. The voltage can then be considered a moisture indicator. In another non-limiting embodiment of the invention, the moisture sensor 85 and/or the cathode 89 as shown in FIG. 3 is connected to one pole 105 of an ammeter 106, and the anode 93 is connected to a second pole 108 of the ammeter 106 (see FIG. 7). As for the moisture sensor 86, the cathode 95 is connected to the pole 108 of the ammeter 106, and the second outer electrode 97 is connected to the pole 108 of the ammeter 106. The current through the circuit completed by the ammeter, the electrochemical cell and the connecting leads 111 and 112 is measured. As the electrolyte absorbs moisture above the threshold determined by the material choices, the voltage between the anode and the cathode increases from near zero to a characteristic voltage determined by the materials selections and the current through the ammeter increases. The load in the ammeter can be selected to maximize discrimination of the signal. In another non-limiting embodiment of the invention, the features of the potentiometer and ammeter can be combined in a multi-meter 106 to simultaneously record the voltage, current and thus the calculated power delivered by the sensing element to the measurement system. Measuring the voltage and current changes for the moisture adsorption in the electrolyte provides a graph of voltage, current, instantaneous power and the cumulative work performed by the cell vs moisture adsorption that can be used to measure the moisture adsorbed by the electrolyte.

The invention is not limited to the circuit employed to measure the electrical voltage changes when moisture is absorbed by the electrolyte. Shown in FIG. 7 is a non-limiting embodiment of an electrical system 110 that can be used with the moisture sensors 85-88 to determine moisture penetration between layers and/or sheets of in the windshield 20. In the following discussion, the invention will be discussed using the moisture sensor 85 shown in FIG. 3. Unless indicated otherwise, the discussion of the invention using the sensor 85 is applicable to the practice of the invention using the sensors 86 and 87. In the non-limiting aspect, of the invention shown in FIG. 7, the moisture sensor 85 is applied to the surface 23 of the glass sheet 22 and secured against the surface 23 of the first glass sheet 22 in any usual manner, e.g. but not limiting to the invention by the first urethane interlayer 28 (see FIG. 1). As can be appreciated, the coaxial moisture sensor 85 can be integrated in any plastic laminate member (28, 26 and 34). In the non-limiting embodiment of the invention shown in FIG. 7, the coaxial moisture sensor 85 is mounted over the surface 23 of the first glass sheet 22 of the windshield 20 and extends around substantially the entire marginal edges of the first glass sheet 22. The coaxial moisture sensor 85 has anode 89 and a wire 111 connecting the anode 89 to the pole 105 of the multi-meter 106, and a cathode designated by the number 93 and a wire 112 connecting the cathode 93 to the pole 108 of the multi-meter 106 to measure the potential supplied by the moisture sensor 85 across the poles 105 and 108 and/or current through the ammeter or multi-meter 106. In FIG. 7 there is shown a separation between the ends 113 and 114 of the sensor 85. The separation between the ends 113 and 114 is not limiting to the invention, and the ends 113 and 114 of the sensor 85 can overlap one another as shown in phantom in FIG. 7.

The multi-meter 106 of the electrical system 110 can be any conventional high impedance potentiometer circuit, coulometric circuit, or any practicable combination thereof, to measure the output of moisture sensor 85. A control mechanism 116, such as embedded electronics or software on a computer, is used to control and communicate with both the multi-meter 106 and the electrical measurement mechanism 115. The control mechanism 116 can be used to command the multi-meter 106 to provide a specifically set load to the moisture sensor 85 and, after application, the control mechanism 116 can collect and/or calculate the electrical potential and/or current of the moisture sensor 85. All of the multi-meter 106 and the control mechanism 116 can be combined in a single unit or instrument, e.g. a console of the type shown in FIG. 18 of, and disclosed in, U.S. Pat. No. 8,155,816B2 or can be individual units as shown in FIG. 7. The electrical measurement system can be any commonly used system used for measuring potential or current, two such examples are described below for completeness.

In one non-limiting embodiment of the invention, a 1 ohm fixed load is placed on across connection points 89 and 93 and inbetween leads 111 and 112. In this case, 106 is a volt meter monitoring the voltage across the load which directly indicates the current flowing through the load. In the case of zero moisture at the sensor, a reading of zero volts would occur. As moisture ingresses into the laminate and diffuses towards the sensor, the electrolyte increases ionic conduction and allows a current to flow across the load. The current flowing through the load connected between points 89 and 93 result in a voltage to be measured at volt meter 106 directly related to the amount of moisture absorbed in the electrolyte, which is directly proportional to the moisture content of the laminate in direct contact with the moisture sensor. To reduce electrical noise, one conductor can be connected to the circuit ground (93 in the case of sensor type 85 and either conductor in the case of sensor type 86).—In another non-limiting embodiment of the invention a set of electronics are connected to the moisture sensor with no external power supply. When the moisture content of the moisture sensor reaches a sufficient level, the electrolyte allows a sufficient voltage and current to power the connected electronics 106. These electronics send a signal to the logging electronics 116 indicating that a moisture threshold has been reached. The invention described can use the above described methods, or any other potentiometric or coulometric measurement systems including, but not limited to coulomb counters, transistor based, resistive, inductive, hall effect, light emission, electromagnetic sensors, transducer, etc. Additionally the invention can use a combination of voltage and/or current measurement systems at the same time, sequentially, or selectively based on the measurement condition.

More particularly, when moisture penetrates the windshield 20, the moisture will eventually reach the electrolyte 91 of the moisture sensor 85 and/or the electrolyte 99 of the moisture sensor 87. As the moisture reaches the electrolyte 91 and/or 99 of the moisture sensor 85 and/or 87, respectively, the moisture is absorbed by the electrolyte. As the electrolyte absorbs moisture, the voltage across electrolyte 91 and/or 99 increases. As discussed above, the voltage between the cathode and anode of the device is associated with a liquid content of the electrolyte that is associated with the moisture content of the plastic plies 26 and 28. The absolute moisture content of the electrolyte depends on the thickness, and absorption coefficient, of the electrolyte, as well as the moisture content of the interlayer in the immediate vicinity of the moisture sensor. In the practice of a non-limited aspect of the invention, when the measured voltage and/or current of the moisture sensor 85 and/or 87 is at a predetermine value indicating that moisture absorption by the electrolyte 91 and/or 99 is at a predetermined value, the control mechanism 116 sends a signal to the alarm 118 to advise the crew of the aircraft and/or other personnel as disclosed in U.S. Pat. No. 8,155,816B2 of a moisture penetration issue. In another non-limiting embodiment of the invention, the moisture content of moisture sensor 85 and/or 87 is monitored (either continuously or intermittently) and the trending of moisture content over time is analyzed to advise the crew of the aircraft and/or other personnel of an issue with the windshield.

The arrangement of the moisture sensor 85 shown in FIG. 3 can be used to indicate that moisture has penetrated through or around the sealant 36 and entered the volume between the glass sheets 22 and 30 (see FIG. 1). However using a single strip, 104, of the moisture sensor 85 and 87, does not indicate where the moisture penetration occurred, how far the moisture has penetrated, or which side of the windshield the moisture has penetrated. In order to enhance identifying the moisture penetration areas between the glass sheet 22 and the vinyl interlayer 26, multiple strips 104 can be placed in a grid or array pattern over the inner surface 23 of the sheet 22. In the practice of the invention, the anode dissolves, however, the percent dissolution should be within the bounds of the sensor.

Figure 8:
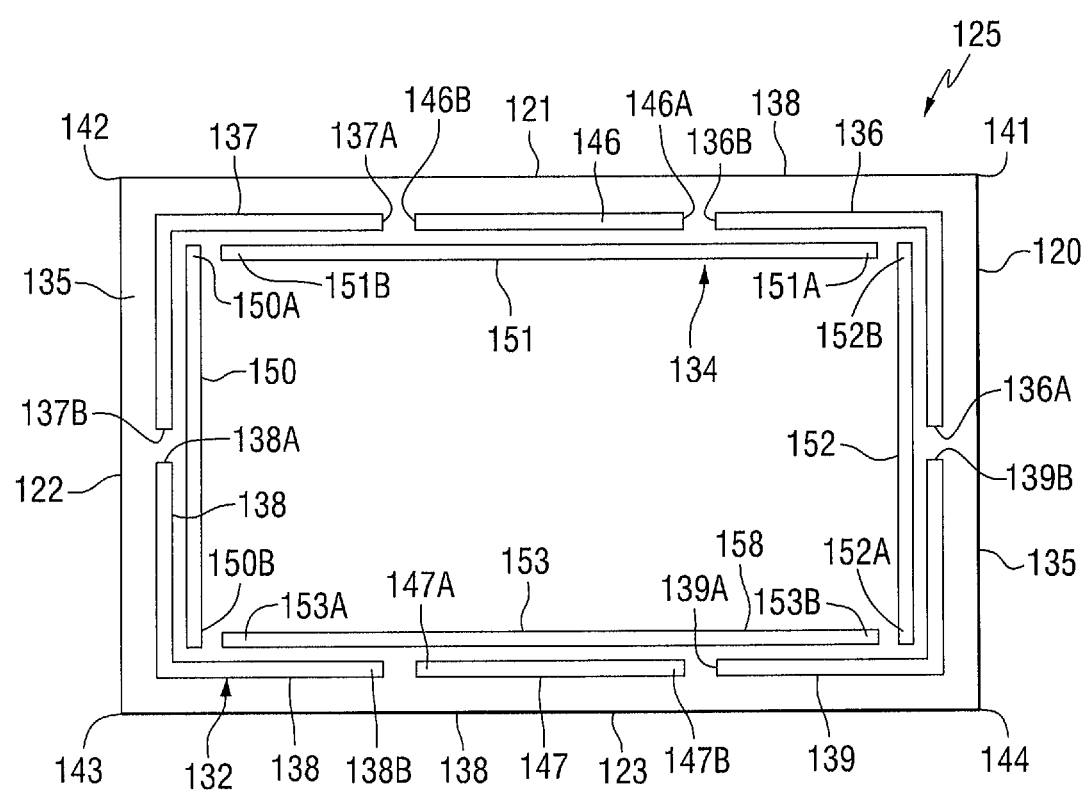
FIG. 8 is a plan view of a non-limiting embodiment of an arrangement of moisture sensors or detectors to estimate approximate position of moisture penetration and depth of moisture penetration.

In the non-limited embodiment of the invention shown in FIG. 8, each one of sides 120-123 of glass sheet 125 has two rows 132 and 134 of moisture sensors at or adjacent to the margin 135 of glass sheet 125 to provide an array of moisture sensors to more definitively identify where a moisture area in the windshield is present. Although the non-limited embodiment of the invention under discussion references the sheet 125 (FIG. 8), the discussion is applicable to the glass sheets 22 and 30, the vinyl interlayer 26 and urethane interlayers 28 and 34 unless indicated otherwise. Further, although reference in the following discussion is made to moisture sensors having different number designations, unless indicated otherwise the moisture sensors mentioned below include the moisture sensor 85 of FIG. 3 and moisture sensor 87 of FIG. 4.

With reference to FIG. 8, the first row 132 of moisture sensors 136-139 are at corners 141-144, respectively of the sheet 125, and moisture sensors 146 and 147 are at the sides 121 and 123, respectively of the sheet 125. End 136A of the moisture sensor 136 is adjacent to and spaced from end 139B of the moisture sensor 139 at the side 120 of the sheet 125; end 136B of the moisture sensor 136 is spaced from and adjacent to end 146A of the moisture sensor 146, and end 146B of the moisture sensor 146 is adjacent to and spaced from end 137A of the moisture sensor 137, at the side 121 of the sheet 125; end 137B of the moisture sensor 137 is adjacent to and spaced from the end 138A of the moisture sensor 138 at the side 122; end 138B of the moisture sensor 138 is adjacent to and spaced from end 147A of the moisture sensor 147, and end 147B of the moisture sensor 147 is adjacent to and spaced from end 139A of the moisture 139, at the side 123, of the sheet 125.

The second row 134 of the moisture sensors includes moisture sensors 150-153. The moisture sensor 150 extends between sides 121 and 123 of the glass sheet 125; has its end 150A adjacent to and spaced from end 151B of the moisture sensor 151, and its end 150B adjacent to and spaced from end 153A of the moisture sensor 153. The moisture sensor 151 extends between sides 122 and 120 of the glass sheet 125 and has its end 151A adjacent to and spaced from end 152B of the moisture sensor 152. The moisture sensor 152 extends between sides 121 and 123 of the glass sheet 125 and has its end 152A adjacent to and spaced from end 153B of the moisture sensor 153. The moisture sensor 153 extends between sides 120 and 122 of the glass sheet 125 and has its end 153B adjacent to and spaced from end 152A of the moisture sensor 152.

The ends A and B of each of the moisture sensors 136-139, 146, 147 and 150-153 are individually electrically connected to the electrical power source 106 as shown in FIG. 7 to apply an electrical potential to the moisture sensors 136-139, 146, 147 and 150-153, and to the electrical measurement mechanism 115 for measuring the electrical potential across and/or the current through the moisture sensors 136-139, 146, 147 and 150-153. In another aspect of the invention, the end A or B of each of the moisture sensors 136-139, 146, 147 and 150-153 are individually electrically connected to the multi-meter 106 as shown in FIG. 7 to measure the potential across and/or the current through the moisture sensors 136-139, 146, 147 and 150-153. The control mechanism 116 controls and communicates with both the multi-meter 106 as discussed above to command the operation of 106 to provide a predetermined or specifically set electrical impedance to the anode and cathode 89 and 93, respectively of the moisture sensor 85 and/or anode 97 and cathode 95 of the moisture sensor 86 and to the anodes and cathodes of the moisture sensors 136-139, 146, 147 and 150-153 and, after application, the control mechanism 116 can collect and/or calculate the electrical potential across and/or the current through the moisture sensors 85, 86, 87, 100, 136-139, 146, 147 and 150-153. The multi-meter 106 and the control mechanisms 116 for the moisture sensors 85, 85, 87, 100, 136-139, 146, 147 and 150-153 can be combined in a single unit or instrument, e.g. a console of the type disclosed in U.S. Pat. No. 8,155,816B2, or can be individual units.

With continued reference to FIG. 6, the arrangement of the two rows 132 and 134 each having spaced moisture sensors, e.g. moisture sensors 136-139, 146 and 147 in the row 132, and the moisture sensors 150-153 in the row 134 provides for a closer approximation to area of moisture penetration. More particularly and not limiting to the invention, moisture is absorbed by the electrolyte 91 and/or 99, positioning moisture penetration 156 in the center area of the side 121 of the sheet 125; moisture is absorbed by the moisture sensors 139 and 153, positioning the moisture penetration 158 in the side 123 adjacent the side 138 of the sheet 125.

The moisture sensors 85-88 can be applied to a surface of one or more of the glass sheets 22 and 30. As is appreciated, when moisture sensors of the invention are placed on more than one sheet, each one of the moisture sensors preferably has its own multi-meter 106, or one multi-meter is provided and is electrically connected to two or more of the moisture sensors through a switching mechanism. Similarly, one or control mechanisms 116 can be used to read and measure the electrical potential or current flowing through each of the moisture sensors on the glass sheets 22 and 30, and the vinyl interlayer 28, of the windshield 20. In this manner the output of each one of the moisture sensors on the sheets 22, 28 and 30 can be monitored.

Figure 9:
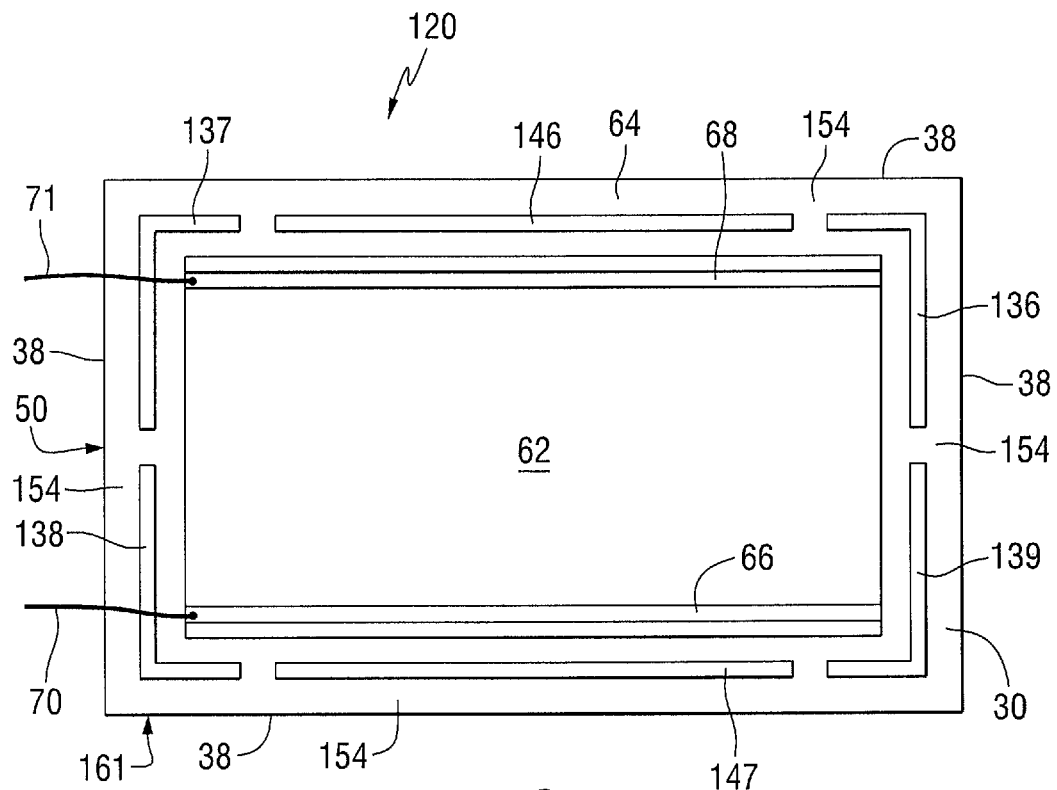
FIG. 9 is a plan view showing the moisture sensor of the invention surrounding the heatable member shown in FIG. 2.

With reference to FIG. 9, there is shown the heatable member 120 having the conductive coating 62 applied to the inner surface 64 of the second glass sheet 30. As can be appreciated by those skilled in the art, the moisture sensors 136-139, 146 and 147 are spaced from the bus bars 66 and 68, and from the conductive coating 62, to electrically isolate the moisture sensors from the bus bars 66 and 68, and from the conductive coating 62, of the heatable member 120. In one non-limiting aspect of the invention, e.g. as shown in FIG. 9, the bus bars are within the Perimeter of the coating 62, and the perimeter of the conductive coating 62 is spaced from sides 38 of the glass sheet 30. The moisture sensors 136-139, 146 and 147 are applied on uncoated portion 154 of the surface 64 of the glass sheet 30 between the sides 38 of the sheet 30 and the conductive coating 62. The uncoated portion 154 of the glass surface 62 can be provided in any convenient manner, e.g. by masking the glass surface during the coating process, or abrasively or chemically removing the coating from the glass surface. Because the glass is chemically strengthened it is preferred to mask the areas during the coating process to avoid surface damage that can cause the tempered glass to fracture.

Figure 10:
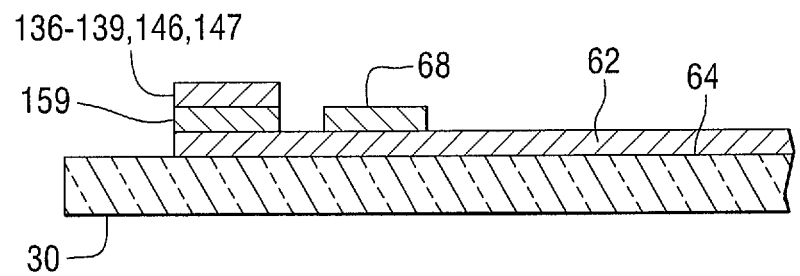
FIG. 10 is an elevated cross sectional side view showing a non-limiting embodiment of the invention for mounting a sensor over a bus bar of a heatable member.
Figure 11:
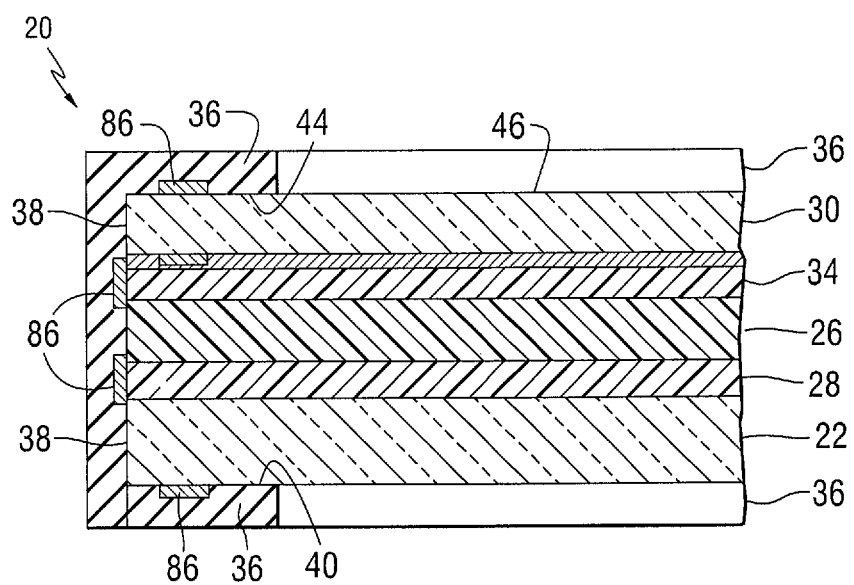
FIG. 11 is a cross section view of a segment of the windshield shown in FIG. 1 showing the position of moisture sensors or detectors at the marginal and peripheral edge portions of the aircraft windshield in accordance to the teachings of the invention.

As can be appreciated, the invention contemplates positioning the anode and cathode of the moisture sensors of the invention over the conductive coating 62 and/or the bus bars 66 and 68. More particularly, as shown in FIG. 10, the anode and cathode of the moisture sensors 136, 139, 145 and 147 are applied over the electrically conductive coating 62. To electrically isolate the anodes 89 and 95, and the cathodes 93 and 97 of the moisture sensors 136, 139, 145 and 147 from the electrically conductive heatable member 62 see FIGS. 9, and 10 respectively one or both the anodes and cathodes of the sensors electrodes 95 and 97 of the moisture sensor 87 shown in FIG. 8 a moisture permeable, electrically nonconductive outer insulator 159 extends under the moisture sensors 136-139, 146 and 147 electrically the coating 62 and moisture sensors 136-139, 146 and 147. Materials that can be used in the practice of the invention, but not limited thereto include nylon (of any chain length), urethane, polyvinyl butyral or polyimide. The layer 159 can have an adhesive layer on each surface to secure one or more of the moisture sensors in position during the handling of the sheets prior to the lamination of the sheets, or can be held in place using any practical means consistent with the practices of laminated windshield manufacture. As can be appreciated, the moisture sensor can decrease visibility through that portion of the glass sheet over which it is deposited, and therefore, for the moisture sensors that extend into the vision area of the windshield, the maximum width of the moisture sensor depends upon the required or specified operator viewing area through the windshield 20. Aircraft transparencies, e.g. windshields have specific safety requirements specifying, among other things, the size of the viewing area of the windshield.

The discussion is now directed to non-limited embodiments of the invention relating to the placement of the non-limiting embodiments of moisture sensors or detectors of the invention on selected components of the windshield 20, to detect the presence of moisture and/or measure the amount of moisture present between the sheets, e.g. but not limited to, between the glass sheets 22 and 30, in accordance to the teachings of the invention.

As critical as the measurement principle and type, where the moisture sensor should be located will determine if the new sensor can effectively detect the moisture ingress and provide early enough warning for the "Intelligent Window" sensor system to alarm the pilot. With reference to FIG. 1 as needed, the placement of the moisture sensor 85 (FIG. 3), the moisture sensor 86 (FIG. 4) and/or the moisture sensor 87 and 88 (FIGS. 5 and 6) can be applied to any position on or between the glass sheets 22 and 30 as shown in FIGS. 1 and 10. Further, the invention is not limited to the number of moisture sensors and/or the location of the moisture sensor on the windshield. More particularly and not limiting to the invention, the moisture sensor can be embedded in the first urethane layer 28 between the glass sheet 22 and the vinyl interlayer 26, embedded in the vinyl interlayer 26; embedded in the second urethane layer 28 between the glass sheet 30 and vinyl interlayer 26.

In the non-limited embodiments of the invention discussed above, the moisture sensors 85, 86 and 87, in general, has the function of measuring the presence and time period that moisture is in contact with the moisture sensor of the invention. The invention, however, is not limited thereto, and the moisture sensor of the invention can be used to measure the presence and time period that moisture is in contact with the moisture sensor and to activate and deactivate electrical equipment, e.g. as discussed below and in U.S. Pat. No. 8,155,816B2.

Control System

Disclosed in U.S. Pat. No. 8,155,816B2, which patent is hereby incorporated by reference, is a method and apparatus to monitor the performance of a transparency, e.g. but not limited to the windshield 20 of the invention and to timely schedule maintenance of, e.g. repairs to, or replacement of, transparencies, e.g. aircraft windshields that are performing outside acceptable limits. In this particular instance, performing outside of acceptable limits as a result of moisture penetration.

In general the output of the sensors carrying data regarding the performance of moisture barrier of the windshield are connected to a console including a computer having software to read and analyze the signals from the moisture sensors or detectors to monitor and/or determine the performance of the windshield. A monitor can be used in the practice of the invention to provide visual display, and a speaker to provide an audio, regarding the performance of the windshield. The console can include an alarm to bring attention to the monitor. Placing the console in the aircraft provides the personnel within the aircraft with real time performance of the windshield.

In another embodiment disclosed in U.S. Pat. No. 8,155,816, the console has a wireless transmitter and receiver; the transmitter transmits signals to a transmitting tower. The signals carry data on the performance of the windshield 20 are transmitted to a control center (not shown). The data received is studied and the appropriate action to be taken is scheduled, e.g., based on the information received, personnel at the control center determine what action, if any, is needed. If action such as repairs to the windshield or replacement of the windshield, is needed, a signal providing a repair schedule is transmitted to the satellite to a maintenance center geographically close to the designated repair location (usually the next scheduled stop for the aircraft) to arrange to have all parts, equipment and personal need at the designated repair location.

The invention is not limited to the embodiments of the invention presented and discussed above which are presented for illustration purposes only and the scope of the invention is only limited by the scope of the following claims and any additional claims that are added to applications having direct or indirect linage to this application.

The invention claimed is:

1. A transparency comprising:
   a plurality of sheets joined together to provide a laminated window having a vision area, the window having a moisture seal on peripheral and marginal edge portions of the sheets;
   a moisture sensor positioned between the sheets and/or between the sheets and the moisture seal, wherein the moisture sensor comprises an electrolyte member comprising at least one of an extruded polymer sleeve and an extruded polymer layer loaded with an electrolyte material, the electrolyte layer being between a first electrode and a second electrode, and wherein the electrolyte material is in ionic contact with the first and second electrodes and maintains the first and the second electrodes spaced from one another and out of surface contact with one another; and
   sensor electronics operatively connected to the electrodes of the moisture sensor to measure a potential between the first electrode and the second electrode and/or to measure a current through the sensor generated by a reaction of the electrolyte material and moisture absorbed by the electrolyte material to determine an amount of moisture absorbed by the electrolyte member, wherein the potential between the first and the second electrode and/or the current through the sensor measures the amount of moisture within the laminated windshield in an area of the moisture sensor.

2. The transparency according to claim 1, wherein the transparency is an aircraft windshield and the sensor electronics measure potential and/or current changes of the electrolyte material in contact with the first and second electrodes due to moisture absorbed by the electrolyte material.

3. The transparency according to claim 2, wherein the electrolyte material is selected from the group of acids comprising sulfuric, hydrochloric, phosphoric, nitric, carboxylic, adipic, mallic, acetic; from organic ligands of the acid and combinations thereof, and from the group of bases comprising sodium hydroxide, potassium hydroxide, lithium hydroxide, magnesium hydroxide, calcium hydroxide and combinations thereof.

4. The transparency according to claim 3, wherein the sensor has a coaxial shape and the electrolyte member has an elongated shape with a center hole,
   the first electrode comprises an annular outside sleeve having a plurality of spaced holes through a wall of the first electrode, and
   the first electrode is in surface contact with an outer surface of the electrolyte material,
   the second electrode comprises a wire positioned within the center hole of the electrolyte material, and
   the electrolyte member is extruded over the wire, such that the second electrode is in surface contact with an inner surface of the electrolyte material.

5. The transparency according to claim 4, wherein the first and the second electrodes are made of a material selected from the group of ruthenium, rhodium, palladium, silver, osmium, iridium, platinum, and gold, and non-noble metals and alloys selected from the group of titanium, chromium, nickel, molybdenum, iron, copper, lead, tin, aluminum, zinc, magnesium, and alloys thereof, and elemental carbon in the form of graphite, carbon black, carbon fiber or grapheme, wherein the elemental carbon is considered a metal and used in the elemental form or as an alloying element with any of the metals recited herein.

6. The transparency according to claim 3, wherein the electrolyte member has an elongated shape having a first surface and a second surface, the first electrode is in electrical contact with the first surface of the electrolyte member and the second electrode is in electrical contact with the second surface of the electrolyte member, and the first and the second electrodes are only electrically connected to one another by way of the electrolyte member and the first electrode and the second electrode each have a plurality of spaced holes extending through their respective walls.

7. The transparency according to claim 6, wherein the first and the second electrodes are made of ruthenium, rhodium, palladium, silver, osmium, iridium, platinum, and gold, and non-noble metals and alloys such as, but not limited to, titanium, chromium, nickel, molybdenum, iron, copper, lead, tin, aluminum, zinc, magnesium, and alloys thereof.

8. The transparency according to claim 6, wherein the electrolyte member has a 4-sided cross section with the first electrode mounted on a side of the electrolyte member designated as the first side of the electrolyte member and the second electrode is mounted on a side of the electrolyte member opposite to the first side.

9. The transparency according to claim 1, wherein the transparency is a laminated aircraft windshield, and the moisture seal overlays marginal edges of outer opposed surfaces of, and peripheral edges, of, the laminated window, and the moisture sensor is between the sheets, and/or between the sheets and the moisture seal, of the laminated aircraft windshield.

10. The transparency according to claim 9, wherein:
the plurality of sheets comprises two or more transparent sheets joined together by an adhesive, and
the moisture sensor is positioned on a surface portion of at least one of the sheets.

11. The transparency according to claim 10, wherein each of the sheets comprises a first major surface opposite to a second major surface and a peripheral surface joining the first major surface and the second major surface, and wherein the surface portion of the at least one of the sheets is selected from the group of the first major surface, the second major surface, the peripheral surface and combinations thereof.

12. The transparency according to claim 9, wherein the moisture sensor is one of a plurality of moisture sensors, wherein a first one of the plurality of moisture sensors is between the moisture seal and the sheets, and a third one of the plurality of moisture sensors is between the moisture seal and outer surface portion of the aircraft transparency.

13. The transparency according to claim 9, wherein the transparency comprises first, second, third, and fourth elongated moisture sensors; each of the moisture sensors comprising a first end and an opposite second end, wherein the first, second, third and fourth moisture sensors are mounted on a major surface of one of the pair of sheets adjacent peripheral edge of the sheet, wherein the second end of the first moisture sensor is adjacent and spaced from the first end of the second moisture sensor, the second end of the second moisture sensor is adjacent and spaced from the first end of the third moisture sensor, the second end of the third moisture sensor is adjacent and spaced from the first end of the fourth moisture sensor, and the second end of the fourth moisture sensor is adjacent and spaced from the first end of the first sensor.

14. The transparency according to claim 13, wherein the first, second, third and fourth moisture sensors form a first boundary and comprising a second boundary within and spaced from the first boundary, and a third boundary within and spaced from the second boundary, wherein each of the second and third boundaries comprises at least one elongated moisture sensor defined as a fifth elongated moisture sensor for the second boundary and as a sixth elongated moisture sensor for the third boundary.

15. The transparency according to claim 1, wherein the transparency is an aircraft transparency and each of the sheets comprises a first major surface opposite to a second major surface and a peripheral surface joining the first major surface, wherein the second surface of the first sheet is in facing relationship to and spaced from the second surface of the second sheet and the sensor element is between the first sheet and the second sheet, and spaced from the peripheral edge of the first sheet and the second sheet.

16. The transparency according to claim 1, wherein the transparency is selected from the group of a laminated aircraft transparency, commercial and residential windows, a window for any type of land vehicle; a canopy, cabin window and windshield for any type of air and space vehicle, a window for any above or below water vessel, and a window for a viewing side or door for any type of containers.

17. The transparency according to claim 16, wherein the sheets of the transparency are selected from the group of uncured plastic sheets, annealed glass sheets, and heat and chemically strengthened, clear, colored, coated uncoated glass sheets, and combinations thereof.

18. The transparency according to claim 1, wherein the first electrode is an anode and the second electrode is a cathode.

19. The transparency according to claim 1, wherein the potential between the first electrode and the second electrode and/or the current through the electrodes is generated by a reaction of the electrolyte material and moisture when moisture is absorbed by the electrolyte material.

20. The transparency according to claim 19, wherein the sensor electronics comprise at least one of a potentiometer for measuring potential and an ammeter for measuring current generated by the reaction of the electrolyte material.

21. The transparency according to claim 1, further comprising a control mechanism configured to:
receive from the sensor electronics information representative of the potential between the electrodes and/or the current through the sensor;
determine the amount of moisture absorbed by the electrolyte member based on the information received from the sensor electronics and a correlation between potential and/or current generated by the moisture sensor and the amount of moisture absorbed by the electrolyte member; and
determine an amount of moisture in materials surrounding the moisture sensor based on the determined amount of moisture absorbed by the electrolyte member.

22. The transparency according to claim 1, wherein the electrolyte material comprises a powdered solid electrolyte mix comprising a weak organic acid and a deliquescent salt selected from the group consisting of chlorides of lithium, calcium, magnesium, zinc, and any combination thereof.

23. A method of making an aircraft transparency having a moisture sensor comprising:
fabricating a laminated aircraft transparency having a moisture barrier over an outer surface of the marginal edges of, and periphery of the laminated aircraft transparency;
during fabrication of the laminated aircraft transparency placing a moisture sensor responsive to moisture between the sheets and/or between the sheets and the moisture seal of the aircraft transparency, wherein the sensor element comprises an electrolyte member comprising at least one of an extruded polymer sleeve and an extruded polymer layer loaded with an electrolyte material between a first electrode and a second electrode, and wherein the electrolyte material is in electrical contact with the first and second electrodes and maintains the first and the second electrodes spaced from one another and out of contact with one another, and
measuring a potential between the first and second electrode and/or a current through the electrodes generated by a reaction of the electrolyte material and moisture absorbed by the electrolyte material to determine an amount of moisture within the laminated windshield in the area of the moisture sensor.

* * * * *